United States Patent [19]

Lin

[11] 4,436,838

[45] Mar. 13, 1984

[54] PROCESS FOR PREPARING ALKANOLS AND ESTERS FROM SYNTHESIS GAS

[75] Inventor: Jiang-Jen Lin, Round Rock, Tex.

[73] Assignee: Texaco Inc., White Plains, N.Y.

[21] Appl. No.: 427,334

[22] Filed: Sep. 29, 1982

[51] Int. Cl.³ .................. C07C 27/06; C07C 29/15
[52] U.S. Cl. ........................... 518/700; 518/714; 502/164
[58] Field of Search ................................ 518/700

[56] References Cited

U.S. PATENT DOCUMENTS 4,362,821  11/1982  Lin .................................. 518/700

*Primary Examiner*—Howard T. Mars
*Attorney, Agent, or Firm*—Robert A. Kulason; Jack H. Park; Richard A. Morgan

[57] ABSTRACT

This invention concerns a process for making alkanols and esters which comprises reacting a mixture of CO and $H_2$ at a pressure of about 500 psig or greater and at a temperature of at least 150° C. in the presence of a catalyst system comprising a ruthenium-containing compound, a second metal from Group IVB, VB, or VIB, consisting of a zirconium, titanium, vanadium or chromium-containing compound and a quaternary phosphonium salt, in the presence of an inert, oxygenated solvent.

24 Claims, No Drawings

PROCESS FOR PREPARING ALKANOLS AND ESTERS FROM SYNTHESIS GAS

BACKGROUND OF THE INVENTION

1. Field of the Invention

This invention concerns an improved process for preparing alkanols and esters by reaction of carbon monoxide with hydrogen in presence of a catalyst system.

2. Prior Art

It has long been known that monofunctional alcohols such as methanol, ethanol, etc. can be formed by the reaction of synthesis gas, i.e., a mixture of carbon monoxide and hydrogen, at elevated pressures of, for example, up to 1000 atmospheres, and at temperatures of from about 200° to 500° C., or more using a mixture of copper, chromium and zinc oxides as catalysts. A wide variety of other catalysts have been employed in the reaction of carbon monoxide and hydrogen to yield liquid products containing substantial amounts of monofunctional alcohols as exemplified by methanol, ethanol, propanol, etc. For example, in U.S. Pat. No. 4,013,700 the reaction of carbon monoxide and hydrogen in the presence of a quaternary phosphonium cation and a rhodium carbonyl complex yields a liquid product having a high methanol content. In U.S. Pat. No. 4,014,913 where the same reactants are contacted with a solid catalyst comprising a combination of rhodium and manganese the product formed contains substantial amounts of ethanol and in U.S. Pat. No. 4,197,253 where the reaction of carbon monoxide and hydrogen is conducted in the presence of a rhodium carbonyl complex and a phosphine oxide compound the resulting product contains a high concentration of methanol. Likewise, when the same reactants are contacted with a rhodium carbonyl complex and a copper salt a liquid product containing a substantial amount of methanol is formed. In U.S. Pat. Nos. 4,332,914 and 4,332,915 where the reaction of carbon monoxide and hydrogen is conducted with a ruthenium catalyst and a cobalt, rhenium or manganese co-catalyst dispersed in a low melting quaternary phosphonium salt, a wide spectrum of alkanol and ester products were produced.

One serious problem associated with synthesis gas operations in the past has been the non-selectivity of the product distribution since high activity catalysts generally yield a liquid product containing numerous hydrocarbon materials. Thus, complicated recovery schemes are necessary to separate the desired products and the overall yield of the valuable organic products is low. There is a definite need in the art for a process which will produce alkanols with a high degree of selectivity from synthesis gas.

This invention therefore is to provide a process of making alkanols and esters by resort to a unique catalyst system which produces said alkanols and esters in good yields.

SUMMARY OF THE INVENTION

This invention concerns a method for making alkanols and esters which comprises reacting a mixture of CO and $H_2$ at a pressure of about 500 psig or greater and at a temperature of at least 150° C. in the presence of a catalyst system comprising a ruthenium-containing compound, a second metal from Group IVB, VB or VIB consisting of a zirconium, titanium, vanadium or chromium-containing compound and a quaternary phosphonium salt, in the presence of an inert, oxygenated solvent.

The selectivity of the reaction of this invention to alkanol and ester production can be further improved in many instances by including in the catalyst system a small amount of dicobalt octacarbonyl.

DETAILED DESCRIPTION OF THE INVENTION

In the narrower and more preferred practice of this invention, alkanols and esters are prepared by reacting a mixture of CO and $H_2$ at a temperature of about 180° to about 250° C. and at a pressure of about 2000 psig or greater in the presence of a catalyst system comprising one or more ruthenium-containing compounds, one or more zirconium, titanium, vanadium or chromium-containing compounds and a quaternary phosphonium salt in the presence of an inert, oxygenated solvent such as 1,4-dioxane, optionally containing a cyclopentadienyl ligand and optionally in the presence of a small amount of dicobalt octacarbonyl.

The catalyst system employed in the practice of this invention contains one or more ruthenium-containing compounds and a second metal catalyst from group IVB, VB or VIB together with a quaternary phosphonium salt. The ruthenium-containing catalyst as well as the second metal catalyst may be chosen from a wide variety of organic or inorganic compounds, complexes, etc., as will be shown and illustrated below. It is only necessary that the catalyst precursor actually employed contain the said metals in any of their ionic states. The actual catalytically active species is then believed to comprise ruthenium and zirconium or titanium, vanadium or chromium in complex combination with, for example, tetraalkylphosphonium bromide as well as carbon monoxide and hydrogen.

The ruthenium catalyst precursors may take many different forms. For instance, the ruthenium may be added to the reaction mixture in an oxide form, as in the case of for example, ruthenium(IV) oxide hydrate, anhydrous ruthenium(IV) dioxide and ruthenium(VIII)-tetraoxide. Alternatively, it may be added as the salt for a mineral acid, as in the case of ruthenium(III) chloride hydrate, ruthenium(III) bromide, ruthenium(III) iodide, tricarbonyl ruthenium(II) iodide, anhydrous ruthenium-(III) chloride and ruthenium nitrate, or as the salt of a suitable organic carboxylic acid, for example, ruthenium(III) acetate, ruthenium naphthanate, ruthenium valerate and ruthenium complexes with carbonyl-containing ligands, such as ruthenium(III) acetylacetonate. The ruthenium may also be added to the reaction zone as a carbonyl or hydrocarbonyl derivative. Here, suitable examples include triruthenium dodecacarbonyl and other hydrocarbonyls such as $H_2Ru_4(CO)_{13}$ and $H_4Ru_4(CO)_{12}$, and substituted carbonyl species such as the tricarbonylruthenium(II) chloride dimer, $[Ru(CO)_3Cl_2]_2$.

Preferred ruthenium-containing compounds include oxides of ruthenium, ruthenium salts of an organic carboxylic acid and ruthenium carbonyl or hydrocarbonyl derivatives. Among these, particularly preferred are ruthenium dioxide hydrate, ruthenium tetraoxide, anhydrous ruthenium(IV) oxide, ruthenium acetate, ruthenium(III) acetylacetonate, and triruthenium dodecacarbonyl.

The zirconium and titanium metal catalyst precursors of Group IVB may take many different forms. For instance, the zirconium or titanium may be added to the reaction mixture as a halide, as for example, in the case of zirconium chloride, zirconium iodide, zirconium bromide, titanium chloride, titanium bromide and titanium iodide. Also, cyclopentadienyl ligands may be used with the carbonyl halides of zirconium and titanium. For example, zirconium and titanium-containing compounds in this process include cyclopentadienyl derivatives such as Cp$_2$TiCl$_2$, CpZrCl$_2$ CpZrHCl$_2$ and CpTiCl$_2$.

It is also possible to add the zirconium or titanium to the reaction mixture in the form of an oxide, salt of mineral acid, carbide, carbonate, carbonyl, or hydrocarbonyl derivative. Other zirconium and titanium-containing compounds include carbonates and complexes of carbonyl-containing ligands, such as, for example, zirconium acetylacetonate.

In another method of the practice of this invention, dicobalt octacarbonyl is used in conjunction with a cyclopentadienyl ligand containing titanium or zirconium chloride as a second transition metal catalyst.

Preferred zirconium and titanium-containing compounds useful in the practice of this invention include zirconium and titanium chlorides and cyclopentadienyl ligands of the same optionally in the presence of dicobalt octacarbonyl. Especially preferred is cyclopentadienyl zirconium chloride.

The vanadium metal catalyst precursors of Group VB may also take many different forms. The vanadium may be added to the reaction mixture as a halide such as vanadium chloride, vanadium iodide and vanadium bromide. In addition, cyclopentadienyl ligands may be used with the halides of vanadium. For example, vanadium-containing compounds used in this process may include cyclopentadienyl derivatives such as bis(-cyclopentadienyl)vanadium, bis(cyclopentadienyl)-vanadium dichloride and cyclopentadienyl vanadium tetracarbonyl.

Alternatively the vanadium may be added to the reaction mixture as the complex of a carbonyl-containing ligand, as in the case of vanadium(III) acetylacetonate, etc.

It is also possible to add the vanadium to the reaction mixture in the form of an oxide, salt of mineral acid, carbide, carbonate, carbonyl, or hydrocarbonyl derivative. Other vanadium-containing compounds include carbonates and complexes of carbonyl-containing ligands.

In another method of the practice of this invention, dicobalt octacarbonyl is used in conjunction with a cyclopentadienyl ligand containing vanadium chloride as a second transition metal catalyst.

Preferred vanadium-containing compounds useful in the practice of this invention include vanadium chloride and cyclopentadienyl ligands of the same optionally in the presence of dicobalt octacarbonyl.

The second chromium metal catalyst precursor of Group VIB may take a variety of forms. For instance, the chromium may be added to the reaction mixture as a halide, as, for example, in the case of chromium chloride, chromium iodide and chromium bromide. Also, cyclopentadienyl ligands may be used with the halides of chromium. For example chromium-containing compounds in this process include cyclopentadienyl derivatives such as bis(cyclopentadienyl)chromium.

Alternatively the chromium may be added to the reaction mixture as the complex of a carbonyl-containing ligand, as in the case of chromium(III) acetylacetonate, etc.

It is also possible to add the chromium to the reaction mixture in the form of an oxide salt of a mineral acid, carbide, carbonyl, or hydrocarbonyl derivative. Other chromium-containing compounds include carbonyls such as benzene chromium tricarbonyl [PhCr(CO)$_3$], chromium carbonyl, toluene chromium carbonyl, mesityl chromium carbonyl, etc.

In another method of the practice of this invention, dicobalt octacarbonyl is used in conjunction with a cyclopentadienyl ligand containing PhCr(CO)$_3$ as a second transition metal catalyst.

Preferred chromium-containing compounds useful in the practice of this invention include chromium complexes of carbonyl-containing ligands or phenyl derivatives of same, such as PhCr(CO)$_3$ and cyclopentadienyl ligands of the same optionally in the presence of dicobalt octacarbonyl.

Quaternary phosphonium salts suitable for use in this invention have the formula:

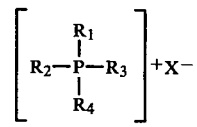

where R$_1$, R$_2$, R$_3$ and R$_4$ are organic radicals, particularly aryl or alkaryl radicals bonded to the phosphorous atom, and X is an anionic species. The organic radicals useful in this instance include those alkyl radicals having 1 to 20 carbon atoms in a branched or linear alkyl chain; they include the methyl, ethyl, n-butyl, iso-butyl, octyl, 2-ethylhexyl and dodecyl radicals. Tetraethyl phosphonium bromide and tetrabutyl phosphonium bromide are typical examples presently in commercial production. The corresponding phosphonium acetates, nitrates, chromates, tetrafluoroborates and other halides, such as the corresponding chlorides, and iodides, are also satisfactory in this instance.

Equally useful are the phosphonium salts containing phosphorus bonded to a mixture of alkyl, aryl and alkaryl radicals. Said aryl and alkaryl radicals may each contain 6 to 20 carbon atoms. The aryl radical is most commonly phenyl. The alkaryl group may comprise phenyl substituted with one or more C$_1$-C$_{10}$ alkyl substituents, bonded to the phosphorus atom through the aryl function.

Illustrative examples of suitable quaternary phosphonium salts include tetrabutylphosphonium bromide, heptyltriphenylphosphonium bromide, tetrabutylphosphonium iodide, tetrabutylphosphonium chloride, tetrabutylphosphonium nitrate, tetrabutylphosphonium chromate, tetrabutylphosphonium tetrafluoroborate and tetrabutylphosphonium acetate.

The preferred quaternary salts are generally the tetraalkylphosphonium salts containing alkyl groups having 1–6 carbon atoms, such as methyl, ethyl and butyl. Tetrabutylphosphonium salts work well and preferred tetrabutylphosphonium salts include the bromide, chloride, iodide, acetate and chromate salts. Tetrabutylphosphonium salts, such as tetrabutylphosphonium bromide, are most preferred for the practice of this invention. Mixtures of these quaternary salts may also be employed if desired.

Generally, in the catalyst system the molar ratio of the ruthenium compound to the quaternary phosphonium salt will range from about 1:1 to about 1:100 or more and preferably, will be from about 1:1.1 to about 1:20. The especially preferred molar ratio is about 1:10.

The quantity of ruthenium compound and the Group IVB, VB or VIB-containing compound employed in the instant invention is not critical and may vary over a wide range. In general, the novel process is desirably conducted in the presence of a catalytically effective quantity of the active ruthenium species and of the zirconium, titanium, vanadium or chromium species which gives the desired product in reasonable yield. The reaction proceeds when employing as little as about $1 \times 10^{-6}$ weight percent, and even lesser amounts, of ruthenium together with about $1 \times 10^{-6}$ weight percent or less of second metal catalyst, basis the total weight of the reaction mixture. The upper concentration is dictated by a variety of factors including catalyst cost, partial pressures of carbon monoxide and hydrogen, operating temperature, etc. A ruthenium concentration of from about $1 \times 10^{-3}$ to about 10 weight percent in conjunction with a zirconium, titanium, vanadium or chromium concentration of from about $1 \times 10^{-3}$ to about 10 weight percent, based on the total weight of reaction mixture is generally desirable in the practice of this invention. The preferred ruthenium-to-second metal catalyst atomic ratio is from about 10:1 to about 0.1:1. The optimum mmole ratio of ruthenium-containing compound to zirconium, titanium, vanadium or chromium-containing catalyst is 1:0.25. Where group IVB metals are used, mixtures such as mixtures of the zirconium and titanium-containing compounds may be employed in the catalyst system if desired.

The choice of a suitable solvent may be important, especially when a large scale, continuous-phase reactor is used. A homogeneous catalyst solution must be obtained so that the continuous feeding of catalyst into the reactor is feasible The solvents useful in the process of this invention are oxygenated hydrocarbons i.e., compounds composed of carbon, hydrogen and oxygen in which the only oxygen atoms present are in ether groups, ester groups, ketone groups or hydroxyl groups of alcohols. Generally, the oxygenated hydrocarbon will contain 3 to 12 carbon atoms. The solvent must be substantially inert under reaction conditions and it must be one which has a normal boiling point of at least 40° C. at atmospheric pressure and preferably the solvent will have a boiling point greater than that of ethanol and other oxygen-containing reaction products so that recovery of the solvent by distillation is facilitated.

Preferred ester-type solvents are the aliphatic and acylic carboxylic acid monoesters as exemplified by butyl acetate, methyl benzoate, isopropyl iso-butyrate and propyl propionate as well as dimethyl adipate. Useful alcohol-type solvents include monohydric alcohols such as cyclohexanol, 1-hexanol, neopentanol, 2-octanol, etc. Suitable ketone-type solvents include, for example, cyclic ketones, such as cyclohexanone and 2-methylcyclohexanone, as well as acyclic ketones such as 2-pentanone, butanone, acetophenone, etc. Ethers which may be utilized as solvents include cyclic, acyclic and heterocyclic materials. Preferred ethers are the heterocyclic ethers as illustrated by 1,4-dioxane and 1,3-dioxane. Other suitable ether solvents include di-n-propyl ether, diethylene glycol dibutyl ether, dibutyl ether, ethyl butyl ether, diphenyl ether, heptyl phenyl ether, anisole, tetrahydrofuran, etc. The most useful solvents of all of the above group include the ethers as represented by monocyclic, heterocyclic ethers such as 1,4-dioxane, etc.

The temperature range which can usefully be employed in these syntheses is a variable dependent upon other experimental factors, including the pressure, the concentration and the choice of the particular species of ruthenium and Group IVB, VB or VIB catalysts, among other things. The range of operability is from about 150° C. to 350° C. when superatmospheric pressure of synthesis gas are employed. A narrow range of 180° to 250° C. represents the preferred temperature range. The most preferred temperature is 220° C.

Superatmospheric pressures of about 500 psi or greater lead to substantial yields of alkanols by the process of this invention. A preferred operating range is from about 4000 psi to about 8000 psi, although pressures above 8000 psi also provide useful yields of the desired alkanols.

As previously pointed out the selectivity of the reaction of this invention to alkanol and ester production can be changed if a small amount of cobalt carbonyl or a derivative thereof like dicobalt octacarbonyl, i.e., from about 0.1 to about 1 moles per mole of the ruthenium-containing compound, is added to the catalyst system.

The relative amounts of carbon monoxide and hydrogen which may be initially present in the syngas, i.e., synthesis gas, mixtures are variable, and these amount may be varied over a wide range. In general, the mole ratio of $CO:H_2$ is in the range about 5:1 to 1:5, although ratios outside these ranges may also be employed. Particularly in continuous operations, but also in batch experiments, the carbon monoxide-hydrogen gaseous mixtures may also be used in conjunction with up to 50 percent by volume of one or more other gases. These other gases may include one or more inert gases such as nitrogen, argon, neon and the like, or they may include gases that may, or may not, undergo reaction under CO hydrogenation conditions, such as carbon dioxide, hydrocarbons such as methane, ethane, propane and the like, ethers such as dimethyl ether, methylethyl ether and diethyl ether, alkanols such as methanol and acid esters such as methyl acetate.

Esters of monocarboxylic acids may also be formed during the course of this alkanol synthesis. Most often these are ester derivatives of acetic acid such as methyl acetate, ethyl acetate, etc. These esters and the individual alkanols formed which include, in addition to methanol, ethanol, propanol and butanol can be conveniently recovered from the reaction mixture by distillation, extraction, etc.

The novel process of this invention can be conducted in a batch, semi-continuous or continuous fashion. The catalyst may be initially introduced into the reaction zone batchwise, or it may be continuously or intermittently introduced into such a zone during the course of the synthesis reaction. Operating conditions can be adjusted to optimize the formation of the desired alkanol product, and said material may be recovered by methods well known in the art, such as distillation, fractionation, extraction and the like. A fraction rich in the ruthenium and zirconium and/or titanium catalyst compounds may then be recycled to the reaction zone, if desired, and additional products generated.

The products have been identified in this work by one or more of the following analytical procedures, viz, gas-liquid phase chromatograph (glc), infrared (ir), mass spectrometry, nuclear magnetic resonance (nmr) and elemental analyses, or a combination of these techniques. Analyses have, for the most part, been by parts in weight; all temperatures are in degrees centigrade and all pressures in pounds per square inch gauge (psig).

Selectivity to individual aliphatic oxygenated products in the crude liquid product has been estimated in this work using the equation:

$$\text{selectively} = X/(100-S) \times 100\%$$

where

X = wt% concentration of the individual products in the crude liquid product as determined by glc.
S = wt% concentration of solvent in the crude liquid product as determined by glc.

The product weight gain was estimated, in grams, as the weight difference between the crude liquid product and the total solvent plus catalysts, charged at the start of the run.

Various embodiments of the process of this invention are illustrated in the following examples which are to be considered not limitative.

COMPARATIVE EXAMPLE I

This example illustrates a synthesis of a mixture of alkanols and esters where the reaction of carbon monoxide and hydrogen is catalyzed by ruthenium together with tetrabutylphosphonium bromide salt and where the reaction is conducted in the presence of 1,4-dioxane.

In the examples following Example I an effect on product selectivity and/or an increase in yield of alkanols and esters will be observed with the use of a second transition metal catalyst.

In Comparative Example I a glass liner was charged with hydrated ruthenium oxide (0.19 g, 1.0 mmole), tetra-n-butylphosphonium bromide (3.4 g, 10 mmoles), and 1,4-dioxane (10 g). The glass liner was placed in a stainless steel reactor and purged of air with hydrogen and carbon monoxide (1:1 molar ratio), then pressured to 1000 psi, and heated to 220° C. The pressure was brought up to 6300 psi and during the reaction period the constant pressure was maintained by using a surge tank. After 18 hours, the reactor was allowed to cool, the excess gas sampled and vented and the liquid products recovered.

The liquid products, which were obtained with 8.5 g weight gain, were analyzed by glc and the following product selectivities (on solvent-free basis) were obtained:

methanol = 43 wt%
ethanol = 24 wt%
n-propanol = 7 wt%
n-butanol = 8 wt%
methyl acetate = 3 wt%
ethyl acetate = 3 wt%
n-propyl acetate = 0 wt%
Catalyst productivity (based on weight gain) = 8500/g-atm-Ru A typical off-gas analysis showed the presence of:
carbon monoxide = 36%
hydrogen = 41%
carbon dioxide = 17%
methane = 3.4%

The water content, analyzed by Karl-Fischer titration, was 0.75% in the liquid product.

It is realized that methanol is the major component in the liquid product distribution and the ratio of methanol to ethanol is about 1.8:1 (43 wt% vs 24 wt%).

EXAMPLE 2

A glass liner was charged with hydrated ruthenium oxide (0.19 g, 1 mmole), tetra-n-butyl phosphonium bromide (3.4 g, 10 mmole), cyclopentadienyl hydridozirconium chloride (0.065 g, 0.25 mmole) and 10 g p-dioxane. The glass liner was placed in a stainless steel reactor. The reactor was purged of air and pressured to 1000 psi with 1:1 ratio of hydrogen and carbon monoxide, then was heated to 220° C., while it was agitated by motor spinning or rocking. The pressure was brought up to 6300 psi. The reaction was stopped after 18 hours and cooled to room temperature. The off-gas was taken by using a steel gas bomb. The gas chromatographic techniques were used for analyzing liquid and gas samples.

The liquid products (weight gain 7.72) were analyzed and the product distributions were calculated to be: (on solvent-free basis)

| | |
|---|---|
| 35% | CH$_3$OH |
| 30% | C$_2$H$_5$OH |
| 4% | n-prOH |
| 2% | n-BuOh |
| 8% | MeOAc |
| 4% | EtOAc |
| 0% | nPrOAc |
| 1.45% | H$_2$O |

It might be noted that the ratio of methanol to ethanol, e.g., 1.16:1 is different from 1.8:1 in Example 1.

EXAMPLES 3–13

A number of additional examples were conducted using the same procedures as in Example 2. A variety of catalysts were employed in these examples and in Examples 10–13 the catalyst system included dicobalt octacarbonyl. Pertinent data relating to these examples are set out in Table I which follows:

TABLE I
Alkanol Production From Carbon Monoxide And Hydrogen

| Example | Catalysts (mmole used) | 1,4-dioxane Solvent (g) | Reaction Conditions | Weight Gain (g) | CH₃OH | C₂H₅OH | n-PrOH | n-BuOH n | MeOAc | EtOAc | n-PrOAc |
|---|---|---|---|---|---|---|---|---|---|---|---|
| 3 | RuO₂/n-Bu₄PBr/Cp₂ZrCl₂ (1: 10: 0.25) | 10 | 6300 psi CO/H₂ = 1:1 220° C. 18 hrs | 8.4 | 32 | 35 | 6 | 4 | 9 | 5 | 0 |
| 4 | RuO₂/n-Bu₄PBr/Zr(acac)₄ (1: 10: 0.25) | 10 | 6300 psi CO/H = 1:1 220° C. 18 hrs | 6.2 | 38 | 27 | 3 | 3 | 8 | 1 | 0 |
| 5 | RuO₂/n-Bu₄PBr/Cp₂TiCl₂ (1: 10: 0.25) | 10 | 6500 psi CO/H = 1:1 220° C. 18 hrs | 7.1 | 33 | 30 | 5 | 2 | 9 | 6 | 0 |
| 6 | RuO₂/n-Bu₄PBB/Cp₂TiCl₂ (1: 10: 0.25) | 10 | 6300 psi CO/H = 1:2 220° C. 16 hrs | 10.4 | 39 | 32 | 5 | 0 | 5 | 3 | 0 |
| 7 | RuO₂/n-Bu₄PPh₃PBr/Cp₂TiCl₂ (1: 10: 0.25) | 10 | 6300 psi CO/H = 1:2 220° C. 18 hrs | 2.75 | 6 | 21 | 8 | 0 | 5 | 3 | 0 |
| 8 | RuO₂/n-BuPh₃PBr/Cp₂TiCl₂ (2: 20: 0.5) | 10 | 8700 psi CO/H = 1:1 220° C. 16 hrs | 6.2 | 10 | 48 | 5 | 2 | 7 | 12 | 4 |
| 9 | RuO/n-C₇H₁₅Ph₃PBr/Cp₂TiCl₂ (1: 10: 0.25) | 10 | 6500 psig CO/H = 1:1 220° C. 16 hrs | 3.1 | 8 | 43 | 5 | 0 | 15 | 15 | 6 |
| 10 | RuO₂/n-Bu₄PBr/Cp₂TiCl₂/Co₂(CO)₈ (1: 10: 0.25 .25) | 10 | 6300 psi CO/H = 1:2 220° C. 18 hrs | 4.9 | 22 | 39 | 8 | 1 | 10 | 13 | 0 |
| 11 | RuO₂/n-Bu₄PBr/Cp₂TiCl₂/Co₂(CO)₈ (1: 10: 0.25 0.25) | 10 | 4000 psi CO/H = 1:1 220° C. 16 hrs | 2.5 | 35 | 28 | 5 | 1 | 9 | 7 | 0 |
| 12 | RuO₂/n-Bu₄PBr/Cp₂TiCl₂/Co₂(CO)₈ (1: 10: 0.25 0.25) | 10 | 6500 psi CO/H₂ = 1:1 220° C. 18 hrs | 9.4 | 13 | 25 | 7 | 0 | 19 | 21 | 4 |
| 13 | RuO₂/n-Bu₄PBr/Cp₂ZrCl₂/Co₂(CO)₈ (1: 10: 0.25 0.25) | 10 | 6300 psi Co/H₂ = 1:1 220° C. 18 hrs | 9.2 | 16 | 26 | 6 | 1 | 24 | 20 | 0 |

In Examples of 2-13, the presence of a second metal, such as Zr, Ti or Co and the variety of phosphonium bromide have a significant effect on product selectivities. The ratio of methanol to ethanol has the range from 1.4:1 (Example 4) to 1:5.3 (Example 9), and the selectivities of ester products ($C_1/C_3$ acetate) can range 9% in Example 4 to 44% in Example 13.

EXAMPLE 14

A glass liner was charged with hydrated ruthenium oxide (0.19 g, 1 mmole) tetra-n-butyl phosphonium bromide 3.4 g, 10 mmole), vanadium chloride (0.039 g, 0.25 mmole) and 10 g p-dioxane. The glass liner was placed in a stainless steel reactor. The reactor was purged of air and pressured to 1000 psi with 1:1 ratio of hydrogen and carbon monoxide, then was heated to 220° C., while it was agitated by motor spinning or rocking. The pressure was brought up to 6120 psi. The reaction was stopped after 18 hours and cooled to room temperature. The off-gas was taken by using a steel gas bomb. The gas chromatographic techniques were used in analyzing liquid and gas samples.

The liquid products were analyzed and the following product selectivities were obtained:

| | | |
|---|---|---|
| $CH_3OH$ | 54% | |
| $C_2H_5OH$ | 14% | |
| n-PrOH | 6.5% | |
| n-BuOH | 7% | |
| MeoAc | 0% | |
| EtoAC | 0% | |

It is noted that $C_1/C_4$ alcohols are major components (ca.81.5%), especially methanol (54%) and esters compounds are minimized in this catalyst system.

EXAMPLE 15

A glass liner was charged with hydrated ruthenium oxide (0.19 g, 1 mmole) tetra-n-butyl phosphonium bromide (3.4 g, 10 mmole), benzene chromium tricarbonyl (0.054 g, 0.25 mmole) and 10 g p-dioxane. The glass liner was placed in a stainless steel reactor. The reactor was purged of air and pressured to 1000 psi with 1:1 ratio of hydrogen and carbon monoxide, then was heated to 220° C., while it was agitated by motor spinning or rocking. The pressure was brought up to 8000 psi. The reaction was stopped after 18 hours and cooled to room temperature. The off-gas was taken by using a steel gas bomb. The gas chromatographic techniques were used for analyzing liquid and gas samples.

The liquid products (weight gain 8.2 g) were analyzed and the following product selectivities were obtained:

| | | |
|---|---|---|
| $CH_3OH$ | 39% | |
| $C_2H_5OH$ | 28% | |
| n-PrOH | 6% | |
| n-BuOH | 8% | |
| MeOAC | 0% | |
| EtOAC | 4% | |
| n-PrOAc | 0% | |

It is claimed:

1. A process for making alkanols and esters which comprises reacting a mixture of CO and $H_2$ at a pressure of about 500 psig or greater and at a temperature of at least 150° C. in the presence of a catalyst system comprising one or more ruthenium-containing compounds, a second metal catalyst selected from groups IVB, VB or VIB, consisting of a zirconium, titanium, vanadium or chromium-containing compound, and a quaternary phosphonium salt, in the presence of an inert, oxygenated solvent.

2. The process of claim 1 wherein the process is conducted at a pressure of about 4000 psi to about 8000 psi.

3. The process of claim 1 wherein the process is conducted at a temperature of about 180° to about 250° C.

4. The process of claim 1 wherein the process is conducted with a ratio of CO to $H_2$ of about 1:5 to 5:1.

5. The process of claim 1 wherein said quaternary salt is a tetraalkylphosphonium salt.

6. The process of claim 5 wherein said alkyl groups contain 1-6 carbon atoms.

7. The process of claim 6 wherein said quaternary salt is a tetrabutylphosphonium salt.

8. The process of claim 7 wherein said tetrabutylphosphonium salt is selected from the group consisting of tetrabutylphosphonium bromide, tetrabutylphosphonium chloride, tetrabutylphosphonium iodide, tetrabutylphosphonium acetate and tetrabutylphosphonium chromate.

9. The process of claim 8 wherein the said tetrabutylphosphonium salt is tetrabutylphosphonium bromide.

10. The process of claim 1 wherein the ruthenium-containing compound is selected from the group consisting of one or more oxides of ruthenium, ruthenium salts of an organic carboxylic acid, ruthenium complexes with carbonyl-containing ligands and ruthenium carbonyl or hydrocarbonyl derivatives.

11. The process of claim 10 wherein the said ruthenium-containing compound is selected from the group consisting of anhydrous ruthenium(IV) dioxide, ruthenium(IV) dioxide hydrate, ruthenium(VIII) tetraoxide, ruthenium acetate, ruthenium propionate, ruthenium(III) acetylacetonate and triruthenium dodecacarbonyl.

12. The process of claim 11 wherein said ruthenium-containing compound is ruthenium(IV) dioxide.

13. The process of claim 1 wherein the said zirconium-containing compound is selected from the group consisting of zirconium carbonyl, zirconium(IV) oxide, zirconium(IV) acetylacetonate, zirconium chloride bis(-cyclopentadienyl)zirconium chloride and bis(cyclopentadienyl)hydridozirconium chloride.

14. The process of claim 13 wherein the said zirconium-containing compound is bis(cyclopenadienyl) zirconium chloride.

15. The process of claim 1 wherein the said titanium-containing compound is selected from the group consisting of titanium carbonyl, titanium(IV) acetylacetonate, titanium tetrachloride, titanium dioxide, titanium-(IV) acetate, cyclopentadienyltitanium trichloride, titanocene dichloride and bis-cyclopentadienyl titanium chloride.

16. The process of claim 15 wherein the said titanium-containing compound is bis-cyclopentadienyltitanium chloride.

17. The process of claim 1 wherein the said vanadium-containing compound is vanadium(III) chloride, vanadium carbonyl, or vanadium(III) acetylacetonate.

18. The process of claim 1 wherein the said chromium-containing compound is benzene chromium tricarbonyl, chromium carbonyl, or chromium(III) acetylacetonate.

19. The process of claim 1 wherein the zirconium, titanium, vanadium or chromium-containing compound is used in conjunction with a cyclopentadienyl ligand.

20. The process of claim 19 wherein said catalyst system also contains dicobalt octacarbonyl.

21. The process of claim 1 wherein said ruthenium-containing compound is ruthenium(IV) oxide, said quaternary phosphonium salt is tetra-n-butylphosphonium bromide and said zirconium-containing compound is cyclopentadienyl zirconium chloride.

22. The process of claim 1 wherein said ruthenium-containing compound is ruthenium(IV) oxide, said quaternary phosphonium salt is tetra-n-butylphosphonium bromide and said titanium-containing compound is cyclopentadienyl titanium chloride.

23. The process of claim 1 wherein the said solvent is selected from the group consisting of 1,3-dioxane, 1,4-dioxane and diphenyl ether.

24. The process of claim 1 wherein the said solvent is 1,4-dioxane.

* * * * *